United States Patent [19]

Cusumano

[11] 3,956,191

[45] May 11, 1976

[54] METHOD FOR MAKING BIMETALLIC CATALYSTS

[75] Inventor: James A. Cusumano, Rahway, N.J.

[73] Assignee: Exxon Research and Engineering Company, Linden, N.J.

[22] Filed: May 2, 1974

[21] Appl. No.: 466,168

[52] U.S. Cl. .............................. 252/474; 252/476; 260/348.5 R
[51] Int. Cl.² ........................................ B01J 23/66
[58] Field of Search ...................... 252/474, 476; 260/348.5 R; 75/109; 427/126, 436

[56] References Cited
UNITED STATES PATENTS

| | | | |
|---|---|---|---|
| 2,836,515 | 5/1958 | McNally | 427/436 X |
| 3,144,416 | 8/1964 | Hosoda et al. | 252/476 |
| 3,709,681 | 1/1973 | Wilson | 75/109 |
| 3,844,981 | 10/1974 | Cusumano | 252/476 X |

*Primary Examiner*—W. J. Shine
*Attorney, Agent, or Firm*—Robert J. Baran

[57] ABSTRACT

The instant invention relates to a novel method for preparing novel multimetallic catalysts which comprises contacting a catalyst comprising a first metal with a solution of a second metal, said second metal is selected to be lower in the electrochemical series than said first metal and the contacting conditions are adjusted so that a portion of said first metal is displaced by said second metal. This novel technique is believed to form catalysts characterized as containing surface alloys or multimetallic clusters of said first and second metals. The first metal may be present as a supported metal or alternatively may be a metallic powder.

6 Claims, 1 Drawing Figure

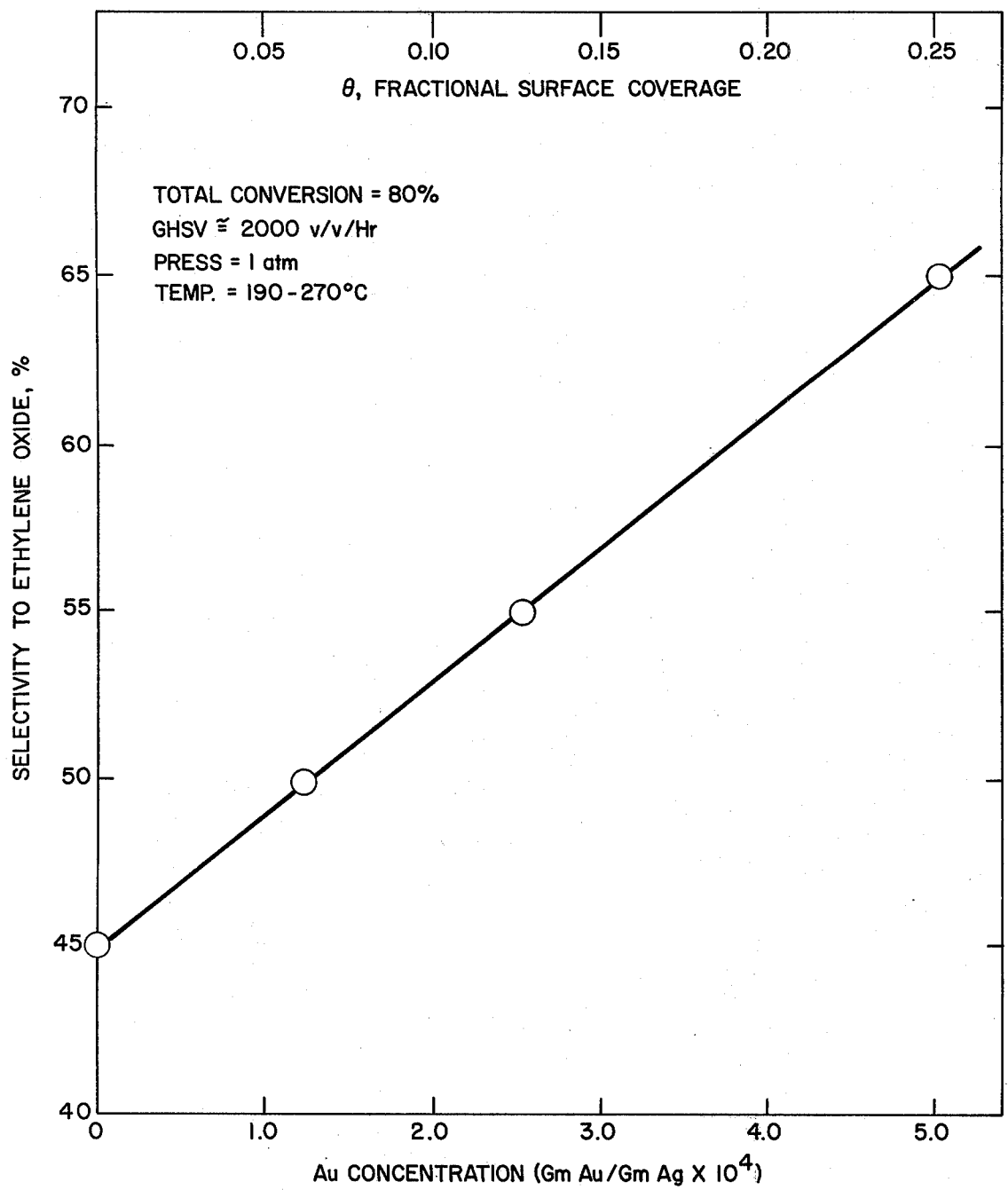

METHOD FOR MAKING BIMETALLIC CATALYSTS

FIELD OF THE INVENTION

The instant invention relates to a novel method for preparing novel multimetallic catalysts which comprises contacting a catalyst comprising a first metal with a solution of a second metal, said second metal is selected to be lower in the electrochemical series than said first metal and the contacting conditions are adjusted so that a portion of said first metal is displaced by said second metal. The second metal covers only a fraction $\theta$ of the surface of the first metal where $0 < \theta < 1.0$, preferably $0.01 < \theta < .5$. This novel technique is believed to form catalysts characterized as containing surface alloys or multimetallic clusters of said first and second metals. The first metal may be present as a supported metal or alternatively may be metallic powder. In one preferred embodiment a Ag metal powder is contacted with an aqueous $AuCl_4$-containing solution at conditions whereby a portion of the surface Ag atoms are replaced by Au atoms. This particular catalyst is especially useful as an ethylene oxidation catalyst in processes wherein ethylene is converted to ethylene oxide in the presence of oxygen. In a second preferred embodiment a supported Ni-Cu alloy is prepared by replacing surface Ni atoms with Cu atoms from aqueous solution.

BACKGROUND OF THE PRIOR ART

Various heterogeneous multimetallic catalysts have come into commercial acceptance for chemical and petroleum processes previously utilizing monometallic catalysts. For example, see U.S. Pat. No. 3,769,201, Catalytic Reforming Process, J. H. Sinfelt and A. E. Barnett; U.S. Pat. No. 3,729,408, Catalytic Reforming Process, J. H. Sinfelt and J. L. Carter; U.S. Pat. No. 3,617,518, Inhibition of Hydrogenolysis, J. H. Sinfelt and A. E. Barnett; U.S. Pat. No. 3,567,625, Hydroforming with Promoted Iridium Catalysts, J. H. Sinfelt and A. E. Barnett; U.S. Pat. No. 3,442,973, Isomerization Process Utilizing a Gold-Palladium Alloy in the Catalyst, J. H. Sinfelt, A. E. Barnett and G. W. Dembinski; J. H. Sinfelt, J. L. Carter and D. J. C. Yates, J. Catalysis 24, 283 (1972); J. H. Sinfelt, J. Catalysis 29, 308 (1973).

It has been found that in reforming processes, for example, various results may be obtained with multimetallic catalysts similar to those that could not be obtained with the prior art monometallic catalysts. For example, the cracking activity of platinum on alumina could be modified by using a Group I-B metal in combination with platinum as the active catalyst metal. Various catalytic oxidation multimetallic catalysts are now being utilized. For example, see U.S. Ser. No. 259,929, filed June 5, 1972 in the name of James Cusumano, hereby incorporated by reference, which teaches a silver alloy catalyst used for ethylene oxidation. See also U.S. Pat. Nos. 2,605,239; 3,144,416; 3,664,970; 2,424,083; and 2,143,371, teaching other silver alloy catalysts for the same process.

Multimetallic catalysts have also been used in fuel cell processes. For example, as electrodes, PdRu, PtRu, PdAu, PtPd, PdAg and a host of others have been reported.

In many of the above multimetallic catalysts, the composition of the surface of the metal phase does not correspond to that of the bulk metal. Because the bulk composition has only secondary effects on catalysis, it would be useful to have a means of preparing multimetallic catalysts in which one could control the surface composition while maintaining an essentially pure monometallic phase in the bulk. Such a technique would have the following advantages:

Minimize the need for one constituent in catalyst preparation (especially useful if this constituent were rare or expensive).

Permit control of surface composition and thus control of catalytic activity and selectivity.

For example, it is known in the art that one can achieve dramatic enhancement in selectivity of hydrocarbon conversion reactions by alloying Group I-B metals with Group VIII metals (J. H. Sinfelt, J. L. Carter and D. J. C. Yates, J. Catalysis 24, 283 (1972)). These effects are known to correlate with alloy surface composition. Thus, if one alloys copper with nickel (J. H. Sinfelt, J. L. Carter and D. J. C. Yates, J. Catalysis 24, 283 (1972) or copper with ruthenium (J. H. Sinfelt, J. Catalysis 29, 308 (1973)), the copper inhibits the carbon-carbon bond hydrogenolysis activity of the Ru and Ni but maintains and in some instances promotes, hydrogenation and dehydrogenation reactions. This selectivity phenomena is known to be related and dependent upon surface alloy or cluster composition (J. H. Sinfelt, J. L. Carter and D. J. C. Yates, J. Catalysis 24, 283 (1972); J. H. Sinfelt, J. Catalysis 29, 308 (1973)). However, conventionally one adjusts the surface composition by controlling the bulk composition. This is inefficient as one could achieve the same end results with the use of much less metal by controlling surface composition with the invention described herein.

SUMMARY OF THE INVENTION

This invention relates to a novel method for preparing a multimetallic catalyst which comprises contacting a catalyst comprising a first metal with a solution comprising a second metal which is below said first metal in the electrochemical series, at conditions sufficient to allow a portion of said first metal to be displaced by said second metal on said catalyst. Alternatively, this novel method may be utilized in preparing catalysts where said first metal is above said second metal in the electrochemical series by the application of a voltage to said solution, e.g. as in a battery or a fuel-cell electrode.

In the preferred embodiment of the instant invention, however, the second metal is below said first metal in the electrochemical series. Thus, various catalysts which may be prepared by the instant method may be conveniently determined by reference to the electrochemical series.

While not wishing to be bound by theory it is believed that the novel catalysts prepared by the instant method are characterized as forming surface multimetallic clusters, that is, the second and subsequent metals will form multimetallic clusters or two dimensional "alloys" at the surface of said first metal while a portion of said first metal will pass into the solution. Thus, the instant catalyst will be characterized as having a surface phase containing two or more metals while the bulk phase of said catalyst will comprise said first metal in a substantially pure state. In an analogous fashion one may start with an alloy of two or more metals and use the same technique to displace one or more metals in order to form a multimetallic surface cluster of two or more metals. The catalysts prepared by this novel method are useful in all processes, known in the prior art, which now utilize the multimetallic or alloy catalysts prepared in the prior art manner.

Preferably, the novel method is utilized to prepare bimetallic catalysts. Some examples which are not intended to be limiting are listed in Table 1 below.

TABLE 1

| Bimetallic Catalyst Systems via Electromotive Displacement | |
|---|---|
| Surface Phase | Bulk Phase |
| Au | Pt, Pd, Ni, Cu, Ag, Ru, Ir, Rh |
| Ag | Pt, Pd, Ni, Cu, Rh, Ru |
| Cu | Ni |
| Bulk Phase | Surface Phase |
| Fe | Pt, Pd, Au, Ag, Ru, Ir, Rh |
| Ag | Au, Ir |
| Zn | Pt, Pd, Au, Ag, Ru, Ir, Rh |
| Cu | Pt, Pd, Au, Ag, Ru, Ir, Rh |
| Ni | Pt, Pd, Au, Ag, Ru, Ir, Rh |

In selecting catalysts which may be prepared by reference to Table 1 the bulk phase will be a metal which may be either in the form of a powder or present on a support. In catalysis the metal will usually have a substantially high surface area in order to obtain activity. Thus, for example, the metal powder may vary in surface area from .01 to 100 $m^2/gm$ metal preferably from 1 to 50 $m^2/gm$ metal. Alternatively the metal may be supported on an inert support, e.g. a support selected from the group consisting of refractory materials and activated carbon. Useful support materials include (a) ceramic compositions such as crushed porcelain or fire brick, (b) silicon-based materials such as silica, silica gel, silicon carbide, clays, natural or synthetic silicates such as kieselguhr, kaolin, china clay, attapulgus clay, etc., (c) alumino-silicate zeolite materials such as naturally occurring or synthetic erionite, mordenite, faujasite, etc. that may or may not be previously converted to a hydrogen or ammonia form and reduced in soda content by virtue of an exchange with various metal ions including rare-earth metal cations, (d) refractory inorganic oxides, including alumina, titanium dioxide, zinc oxide, magnesia, thoria, chromia, silica-alumina, alumina-titania, silica-zirconia, aluminachromia, etc. and (e) mixtures of one or more of the materials referred to above.

The bulk phase of the first metal will be contacted with solutions containing the second metal which is intended to be alloyed with said first metal to provide a surface alloy or cluster phase. The second metal will be present in a form which is capable of electrochemically displacing some of the first metal, i.e. the bulk phase. Generally, the second metal will be contacted with the bulk phase as a solution (preferably aqueous) of a salt of said second metal. The salt may contain the metal which will alloy with the bulk phase in either its cation or anionic form, e.g. as in the case of forming a Pd on Ni alloy, bulk Ni powder or supported Ni powder may be contacted with an aqueous solution of either cationic Pd (e.g. $PdCl_2$) or an anionic Pd solution [e.g. $(NH_4)_2PdCl_4$]. Concentration of salt, temperature and pressure as well as pH etc. may be conveniently adjusted to yield the proper surface composition of the catalyst. The contacting times as well may be varied to yield a catalyst having either a large portion or a small portion of the surface atoms of the bulk phase replaced by the second metal.

SPECIFIC EMBODIMENTS OF THE INSTANT INVENTION

Preparation of an Ag-Au Ethylene Oxidation Catalyst

A bulk Ag catalyst with an Ag-Au surface composition may be prepared by electrochemical displacement. First Ag metal is prepared by adding a 50% KOH solution (250 gm KOH in 250 cc distilled $H_2O$) via a burette in 15 minutes to a solution of 454.5 gm $AgNO_3$ and 45 grams of dextrose dissolved in 4500 ml of distilled $H_2O$. The solution is stirred rapidly while adding the KOH solution and then for an additional 45 minutes upon completion of the KOH addition. The solution is then heated to 72°C. and stirred for 45 additional minutes. It is filtered, dried at 110°C., washed with 2 liters of $H_2O$, dried again at 110°C. and washed again with 2 liters of $H_2O$. It is subsequently dried for 72 hours at 120°C. The final product has a surface area of 1 $m^2/gm$ Ag (i.e. a particle size of about 6,000 A).

As an example of the preparation of a bulk Ag catalyst with a surface Ag-Au alloy of controlled composition, a catalyst was prepared in which 6.25% of the Ag surface area was covered with Au. This was done by washing 15 gm of the above prepared Ag powder with 150 cc of $NH_4OH$ (75 cc concession $NH_4OH$ and 75 cc of $H_2O$) and then with 1000 cc of $H_2O$. The powder was then filtered and slurried in 150 cc of $H_2O$ containing $1.88 \times 10^{-3}$ gm Au (as $HAuCl_4$) for 1.5 hours. It was then filtered, and washed with 1000 cc $H_2O$, followed by 150 cc of a solution of $NH_4OH$ (75 cc concentration $NH_4OH$ and 75 cc of $H_2O$). It was again filtered and washed with 1000 cc $H_2O$ and finally dried in air at 110°C. An analysis of the Ag-Au catalyst by atomic fluorescence spectroscopy indicated the only constituents of significance were Ag and Au. Analysis of the final Au solution showed all of the Au was removed from solution and replaced by an equivalent number of silver atoms from the surface of the silver particles. The resultant catalyst consisted of 6,000A particles of Ag with 6.25% of the Ag surface area covered with Au atoms.

Surface Ag-Au alloys prepared by the instant method were tested for ethylene oxidation and found to be very selective catalysts for the formation of ethylene oxide. The data are presented in FIG. 1.

Typically, these catalysts were tested at a GHSV of approximately 2000 v/v/hr at pressures of 1–20 atm and in a temperature range of 150°–300°C. For example, the Ag-Au catalyst with 6.25% of its surface occupied by Au atoms ($1.25 \times 10^{-4}$ gm Au/gm Ag) was tested in a flow reactor by charging 8.6 gms (6.2 cc) of catalyst which was diluted with 3.8 cc of low surface area beads of the same mesh size (20/40). It was heated in a flow of helium (188.1 cc/min) to 200°C. whereupon the oxygen flow (93 cc/min) was turned on for 10 minutes. The ethylene was then allowed to flow at 18.9 cc/min. All flows were at standard conditions (STP). The data are given in Table 2. Similar runs were made for the other Ag-Au compositions at the same conditions. These data are shown in Tables 3 and 4. As one can see from FIG. 1 the selectivity to ethylene oxide (number of moles of ethylene converted to ethylene oxide divided by the number of moles of ethylene converted) at a given conversion level 29 increases linearly with Au surface concentration.

TABLE 2

Oxidation of Ethylene Over Ag-Au Surface Alloy
$\Theta(Au) = 6.25\%$ $(1.25 = 10^{-4}$ gm Au/gm Ag)

| Run No. | Temp °C. | % Conversion | % Selectivity to ETO |
|---|---|---|---|
| 2-1 | 196 | 33.0 | 50.8 |
| 2-2 | 217 | 50.5 | 49.9 |
| 2-3 | 233 | 66.1 | 49.1 |
| 2-4 | 264 | 87.8 | 47.1 |

TABLE 3

Oxidation of Ethylene Over Ag-Au Surface Alloys
$\Theta(Au) = 12.5\%$ $(2.5 \times 10^{-4}$ gm Au/gm Ag)

| Run No. | Temp °C. | % Conversion | % Selectivity to ETO |
|---|---|---|---|
| 3-1 | 216 | 49.2 | 55.3 |
| 3-2 | 234 | 64.0 | 55.8 |
| 3-3 | 257 | 81.3 | 54.2 |
| 3-4 | 268 | 86.1 | 51.4 |

TABLE 4

Oxidation of Ethylene Over Ag-Au Surface Alloys
$\Theta(Au) = 25\%$ $(5.0 \times 10^{-4}$ gm Au/gm Ag)

| Run No. | Temp °C. | % Conversion | % Selectivity to ETO |
|---|---|---|---|
| 7-1 | 196 | 28.2 | 60.2 |
| 7-2 | 216 | 44.7 | 65.5 |
| 7-3 | 234 | 59.5 | 67.6 |
| 7-4 | 252 | 73.2 | 64.1 |
| 7-5 | 265 | 79.2 | 64.0 |

The initial Ag powder for all of these catalysts had a surface area of 1 m²/gm Ag. The surface coverage with Au is readily controlled by the concentration of Au solution which is contacted with the Ag powder. This is because all of the Au is quantitatively displaced from solution up to a surface coverage of 100%. The relationship between surface coverage of Au and Au solution concentration is given in Table 5.

TABLE 5

Relationship Between Au Concentration in
$HAuCl_4$ Solutions and Surface Converage

| Au Concentration (gm Au/gm Ag × 10⁴) | Percent of Ag Surface Covered with Au |
|---|---|
| 1.25 | 6.25 |
| 2.50 | 12.5 |
| 5.00 | 25.0 |

The data for the Ag-Au surface alloys show they are at least as selective to ethylene oxide as the best catalysts known in the art. For example, the data in FIG. 1 are similar to those reported in U.S. Ser. No. 259,929, filed June 5, 1972 in the name of James Cusumano, now U.S. Pat. No. 3,844,981 which also describes a method for preparing Ag-Au alloys. The advantage of the present invention is that it allows one to obtain the same excellent selectivity to ethylene oxide, but minimizes the use of the costly Au component.

The electrochemical displacement phenomenon can also be used to prepare supported multimetallic clusters. If one starts with a well dispersed supported metal in the zero-valent state, because almost all of the metal atoms are exposed, literally all of these atoms are available for displacement in solution by a metal ion which lies above said metal in the electrochemical series. Thus the instant invention was used to prepare a supported Ni-Cu alloy. First a 10 wt. % Ni/SiO₂ catalyst was prepared by impregnating 20.0 gm of Cab-O-Sil HS-5 SiO₂ with 42.0 cc of an aqueous solution containing 11.00 gm of $Ni(NO_3)_2 \cdot 6H_2O$. The catalyst was dried at 110°C. for 16 hrs in a shallow dish. It was then reduced in $H_2$ (1000 cc/min) at 370°C. for 16 hrs and then carefully passivated with dilute air. 2 grams of this 10 wt. % Ni/SiO₂ catalyst was stirred in an aqueous solution of 250 cc of 1M $Cu(NO_3)_2 \cdot 3H_2O$ solution. It was stirred in an inert environment at 30°C. for 12 hrs and then heated to 60°C., held for 10 min and cooled to room temperature. Finally the catalyst was filtered, washed $Cu^{++}$ free with water (test for $Cu^{++}$ with $NH_4OH$) and dried in a filter funnel with ethanol. X-ray diffraction patterns for this material showed a mixture of Ni and Cu metals. The initial 10 wt. % Ni/SiO₂ had a metal surface area of about 22 m²/g catalyst. This corresponds to a catalyst in which the average Ni crystallite size is about 35A corresponding to a dispersion of 33%; i.e. 33% of the Ni atoms are located at the surface of these crystallites. If all of these surface Ni atoms were displaced by Cu atoms the final catalyst would analyze to be 6.52 wt. % Ni and 3.56 wt. % Cu. The actual analysis was 6.01 wt. % Ni and 3.45 wt. % Cu, which indicates that essentially the total Ni surface was covered with Cu atoms. As in the case of the Ag-Au alloy the surface composition is most readily controlled by the concentration of the displacing ion (in this case $Cu^{++}$). Because a very large excess of $Cu^{++}$ ion was used in this instance, complete coverage of the Ni surface is reasonable.

This catalyst was tested and compared to a nickel on silica catalyst and a copper on silica catalyst for cyclopropane hydrogenation which is a model reaction indicating hydrogenolysis activity.

Cyclopropane Hydrogenation

The catalyst charge was 0.1 gm diluted with 1.0 gm of inert porcelain beads. Pretreatment was with $H_2$ at 10 liters/hr at 200°C. for 1/2 hr and then at 370°C. for 1 hr. Three minute cyclopropane pulses were used with the following gas rates and partial pressures:

$H_2$ ($P_{H_2}$=0.20 atm) = 0.5 liter/hr
$C_3H_6$ ($p_A$ = 0.10 atm) = 0.25 liter/hr
He ($P_{He}$ = 0.70 atm) = 1.75 liter/hr
Total = 2.50 liter/hr Cu/10% Ni/SiO₂
(Via Electrochemical Displacement)
Catalyst: 89-A
Run: 15

| Temp °C. | % CH₄ | % C₂H₆ | % C₃H₈ |
|---|---|---|---|
| 25 | nil | nil | 0.8 |
| 52 | .04 | 0.1 | 1.8 |
| 84 | 1.1 | 2.5 | 10.9 |
| 137 | 6.0 | 12.0 | 63.0 |
| 142 | 7.6 | 14.3 | 73.0 |

10% Ni/SiO₂
Catalyst: 88-A-1
Run: 16

| Temp °C. | % CH₄ | % C₂H₆ | C₃H₈ |
|---|---|---|---|
| 25 | nil | nil | nil |
| 50 | .08 | .21 | 1.6 |
| 63 | .47 | 1.0 | 4.3 |
| 93 | 6.0 | 20.0 | 72.0 |

10% Cu/SiO₂
Catalyst: 80-G
Run: 17
No activity in 25–200°C. temp range

Catalyst Preparation

10% Ni/SiO₂

See above.

10% Cu/SiO₂

2.00 gm Cu(NO₃)₂.2H₂O was dissolved in H₂O and diluted to 21.0 cc. Impregnate 10 gm SiO₂ (Cab-O-Sil-HS-5). Dry in air at 110°C. for 16 hr. Reduce at 316°C. for 3 hours. Carefully passivate. X-ray powder pictures show well dispersed Cu metal.

Cu/10% Ni/SiO₂

Slurry 6 gm of 10% Ni/SiO₂ in 250 cc of 1M Cu(-NO₃)₂ solution for 1 hour. Filter and dry at 110°C. for 16 hrs.

This experiment shows the following:
10% Cu/SiO₂ is inactive.
10% Ni/SiO₂ is quite acitve for C-C bond hydrogenolysis.

A surface Cu-Ni alloy is indicated by the much lower activity of the Cu/10% Ni/SiO₂ catalyst for the hydrogenolysis reaction.

Preparation of Ag-Pt Ethylene Oxidation Catalyst

This catalyst was prepared by the Electrochemical Displacement of silver by platinum. Ag metal is prepared by adding a 50% KOH solution (250 gm KOH in 250 cc distilled H₂O) via a burette in 15 minutes to a solution of 454.5 gm AgNO₃ and 45 grams of dextrose dissolved in 4500 ml of distilled H₂O. The solution is stirred rapidly while adding the KOH solution and then for an additional 45 minutes upon completion of the KOH addition. The solution is then heated to 72°C. and stirred for 45 additional minutes. It is filtered, dried at 110°C., washed with 2 liters of H₂O, dried again at 110°C. and washed again with 2 liters of H₂O. It is subsequently dried for 72 hours at 120°C. The final product has a surface area of 1 m²/gm Ag (i.e. a particle size of about 6000A).

A Ag-Pt surface alloy consisting of pure Ag particles with 7% of their surface covered with Pt metal is prepared by washing 15 gm of the above prepared Ag powder with 150 cc of NH₄OH (75 cc conc. NH₄OH and 75 cc of H₂O) and then with 1000 cc of H₂O. The powder was then filtered and slurried in 150 cc of H₂O containing $3 \times 10^{-4}$ gm Pt (as H₂PtCl₆) for 1.5 hours. It was then filtered, and washed with 1000 cc H₂O, followed by 150 cc of a solution of NH₄OH (75 cc conc. NH₄OH and 75 cc H₂O). It was again filtered and washed with 1000 cc H₂O and finally dried in air at 110°C. An analysis of the Ag-Au catalyst by atomic fluorescence spectroscopy indicated the only constituents of significance were Ag and Pt. Analysis of the final Pt solution showed all of the Pt was removed from solution and replaced by an equivalent number of Ag atoms from the surface of the Ag particles. The resultant catalyst consisted of 6000A particles of Ag with 7% of the Ag surface covered with Pt atoms.

The catalyst was used to oxidize ethylene to ethylene oxide in a process run at atmospheric pressure in a flow reactor at a GHSV of about 2000 v/v/hr. The catalyst charge was 9 cc (8–10 gm). The helium, oxygen and ethylene flows were 188.1, 93.0, and 18.9 cc STP/min, respectively. The data are tabulated in Table 6.

TABLE 6

OXIDATION OF ETHYLENE OVER Ag-Pt SURFACE ALLOY
$\Theta(Pt) = 7.0\%$ ($2 \times 10^{-5}$ GM Pt/GM Ag)

| Run No. | Temp. °C. | % Conversion | % Selectivity to ETO |
|---|---|---|---|
| 1 | 192 | 25.3 | 51.2 |
| 2 | 212 | 43.9 | 53.7 |
| 3 | 232 | 70.7 | 54.0 |

This invention has broad application in preparing both supported and unsupported catalysts, and thus has application for preparing catalysts for petroleum processing and chemical conversions and in the fabrication of fuel-cell electrodes. The only requirement for spontaneous reaction is that the electrochemical potential for the sum of all half reactions, E°, be greater than zero. In some instances where the catalytic phase is supported on an electrical conductor (e.g., unsupported metals or fuel-cell electrodes) the instant invention could be used for some reactions for which E°<0 if an applied EMF is used.

What is claimed is:

1. A method for making bimetallic catalysts which comprises contacting a catalyst comprising silver metal, said silver metal being in the form of a powder having a surface area from .01 to 100 m²/g. or present on a refractory metal oxide support, with an aqueous solution comprising a salt of a second metal which is below silver in the electrochemical series whereby a portion of the silver is displaced in the catalyst by said second metal and wherein said second metal is selected from the group consisting of gold, iridium, and platinum.

2. The method of claim 1 wherein said second metal is gold.

3. The method of claim 1 wherein said solution comprises chloroauric acid.

4. The method of claim 1 wherein said solution comprises from $1 \times 10^{-5}$ to $1 \times 10^{-3}$ gm of gold metal as a gold salt for every 1 m² of available silver surface.

5. The method of claim 1 wherein said second metal is platinum.

6. The method of claim 1 wherein said solution comprises H₂PtCl₆.

* * * * *